United States Patent [19]

Wolf et al.

[11] B 4,007,095
[45] Feb. 8, 1977

[54] RECOVERY OF ANHYDROUS DIOXANE EXTRACTIVELY DISTILLED WITH DIOLS OR ALKANOLAMINE

[75] Inventors: Dieter Wolf, Gruenstadt; Eberhard Bender; Theodor Weber, both of Ludwigshafen, all of Germany

[73] Assignee: BASF Aktiengesellschaft, Ludwigshafen (Rhine), Germany

[22] Filed: May 2, 1974

[21] Appl. No.: 466,304

[44] Published under the second Trial Voluntary Protest Program on March 23, 1976 as document No. B 466,304.

[30] Foreign Application Priority Data

May 5, 1973 Germany ............................ 2322709

[52] U.S. Cl. .................................. 203/59; 203/14; 203/64; 203/81; 260/340.6
[51] Int. Cl.$^2$ ............................................ B01D 3/00
[58] Field of Search ................... 203/14, 17, 59, 64, 203/34, 35; 260/340.6, 340.9

[56] References Cited

UNITED STATES PATENTS

| 1,681,861 | 8/1928 | Knorr et al. | 260/340.6 |
| 1,879,637 | 9/1932 | Reid | 260/340.6 |
| 2,072,101 | 3/1937 | Dreyfus | 260/340.6 |
| 2,273,923 | 2/1942 | Bludworth | 203/64 |
| 3,035,060 | 5/1962 | Binning et al. | 260/340.6 |
| 3,310,478 | 3/1967 | Amir | 203/64 |
| 3,584,737 | 6/1971 | Gresselmann | 260/340.6 |

Primary Examiner—Norman Yudkoff
Assistant Examiner—Frank Sever
Attorney, Agent, or Firm—Johnston, Keil, Thompson & Shurtleff

[57] ABSTRACT

Dioxane is produced by reaction of ethylene glycol or a polyethylene glycol using an acid catalyst. The reaction product containing dioxane, water and byproducts is subjected to extractive distillation with a high-boiling agent which is miscible with water.

3 Claims, 1 Drawing Figure

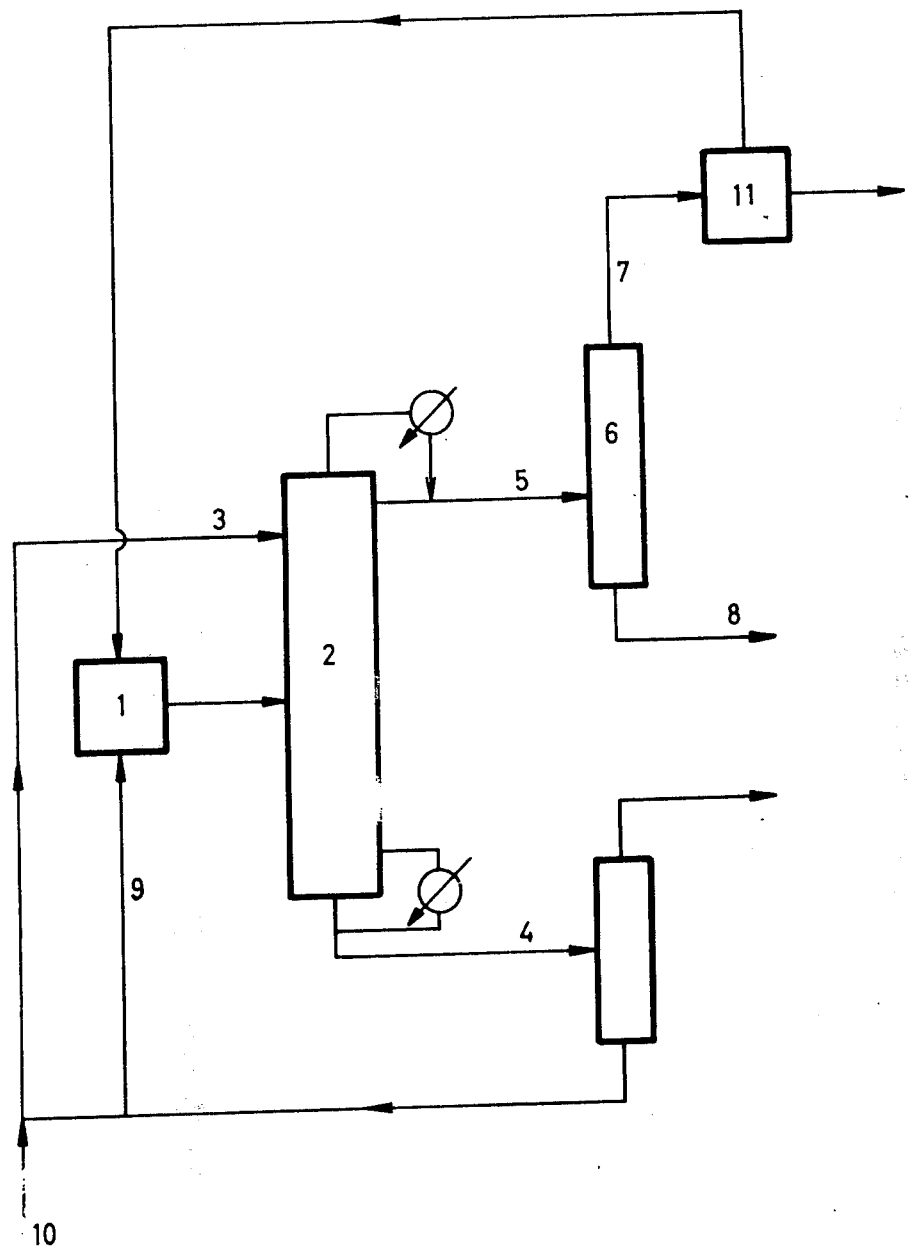

RECOVERY OF ANHYDROUS DIOXANE EXTRACTIVELY DISTILLED WITH DIOLS OR ALKANOLAMINE

This application discloses and claims subject matter described in German Pat. No. P 23 22 709.0 filed May 5, 1973 which is incorporated herein by reference.

1,4-dioxane ("dioxane") is usually produced from ethylene glycol or an oligomer of the same and preferably from diethylene glycol by an acid-catalyzed cyclization reaction at elevated temperature with the elimination of water. Acetaldehyde and the cyclic acetal of acetaldehyde with ethylene glycol (2-methyldioxolane) are formed among others as byproducts.

Technical mixtures formed in the said reaction generally contain from 74 to 78% of dioxane, from 16 to 22% of water, from 2 to 3.5% of 2-methyldioxolane, 0.2 to 1% of acetaldehyde and also small amounts of ethylene glycol and other impurities. The water content of an average of 20% lies in the vicinity of the azeotrope of dioxane with water (17.8% $H_2O$). Methyldioxolane boils at 83°C in the vicinity of the azeotrope of water and dioxane (870°C) and consequently can only be separated with very great difficulty in the presence of water. For this reason the mixture of crude dioxane and water first has to be dehydrated so that pure dioxane can then be recovered by distillation.

Dioxane is usually dehydrated by extracting the mixture of dioxane and water with caustic alkali solution so that a crude dioxane is obtained which contains about 2% of water in addition to the said impurities. When acetaldehyde is present (it is moreover continuously formed by dissociation of 2-methyldioxolane) there is formed by polymerization of acetaldehyde in the caustic alkali solution during the extraction of a resinous residue which rapidly fouls the extraction plant and prevents concentration of the caustic alkali solution for return to the extraction.

It has moreover been found that crude dioxane mixtures which have been obtained by means of sulfuric acid as catalyst also contain sulfur trioxide and possibly also sulfur dioxide which react to form sodium sulfate and make concentration of the caustic alkali solution difficult and its reuse impossible.

It is therefore an object of the invention to provide a process by which anhydrous dioxane can be produced in an economical and industrially simple manner and which is virtually troublefree and poses no waste water problems.

This and other objects and advantages are achieved by a process in which substantially anhydrous dioxane is obtained advantageously from a reaction mixture which contains in addition to dioxane and water minor amounts of 2-methyldioxolane and acetaldehyde by subjecting the reaction mixture to an extractive distillation with a solvent which is miscible with water in all proportions, which does not form an azeotrope with water or with dioxane, which has a higher boiling point than water and which can be separated therefrom by distillation.

Naturally the substantially anhydrous dioxane thus obtained may be further purified by another distillation.

The simplest solvents of the said type are monoethylene glycol and its oligomers having 2 to 5 ethylene glycol units, e.g. diethylene glycol and triethylene glycol which in any case are contained in small amounts in industrial dioxane mixtures. Monopropylene glycol and its oligomers, e.g. dipropylene glycol and tripropylene glycol, propanetriol, propanediol-1,3, the butanediols, e.g. butanediol-2,3 and also alkanolamines such as monoethanolamine, diethanolamine, triethanolamine, mono-, di- and tripropanolamine and technical mixtures of the glycols or alkanolamines with one another are however obviously suitable as solvents for the purposes of the invention.

Naturally it is preferred to use solvents which either do not introduce extraneous substances into the reaction mixture or may be returned to the reaction, i.e. ethylene glycol and its oligomers. In this way the formation of waste products can be avoided in an industrially simple manner. In contrast to the use of caustic soda solution as the dehydrating agent, products which cannot be disposed of completely for example by combustion do not occur at any point in the process.

The FIGURE shows a preferred embodiment of the invention.

The ratio of the proportions of dioxane to solvent is generally from 1:0.1 to 1:100 and particularly from 1:1 to 1:10.

The separation problem can be solved in the following simple manner, with reference to the drawing (FIG. 1):

Reaction mixture formed in a reactor 1 is supplied in the form of vapor or liquid to the middle portion of an extractive distillation column 2 which is charged in the vicinity of its upper end with a solvent according to the invention at 3. The solvent loaded with water and substantially devoid of dioxane is obtained at 4 at the bottoms of the column. Crude dioxane together with the secondary components acetaldehyde and 2-methyldioxolane are obtained in practically anhydrous form and devoid of solvent at the top of the column at 5. By suitable adjustment of the reflux and the amount of solvent added the content of dioxane in the stream 4 and the water content of the crude dioxane in stream 5 may be decreased in any desired manner. It is generally sufficient to deplete the water content in the dioxane to from 1 to 2%.

The overhead from column 2 is separated in a conventional distillation apparatus 6 into acetaldehyde, methyldioxolane, water and a small amount of dioxane (leaving at 7) and pure dioxane (leaving at 8). The mixture of solvent and water obtained in the bottoms of the column 2 is dehydrated by a simple distillation 12 and the solvent is returned through line 9. When monoethylene glycol, diethylene glycol, triethylene glycol or a commercial mixture therefore is used as the solvent it is possible to achieve complete recycling without waste products. In this case the amount of solvent 9 removed from the circulation is chemically transformed into dioxane and has to be replaced by fresh solvent 10.

In connection with the process of the invention it is of interest that the small amount of dioxane contained in stream 7 and the ethylene glycol which is chemically combined in the methyldioxolane should be returned, after thermal dissociation at 11 in the presence of an acid, into reactor 1. Acetaldehyde formed in the dioxolane dissociation 11 can very easily be separated by distillation.

The following additional information is given concerning solvents to be used according to the invention which, as already mentioned, comprise (a) the group of the glycols and (b) certain amines: alkanolamines and particularly monoethanolamine and diethanolamine are especially efficient for the purposes of the extractive distillation and are therefore by no means less suitable as solvents than the other group. Addition of e.g. monoethanolamine to a dioxane/water mixture shifts the vapor pressure of dioxane toward higher values than the addition of e.g. ethylene glycol. Separating columns in this case may be less effective with the same result when ethanolamines are used than with glycols. A solvent may therefore be chosen from group (*a*) or (*b*) depending on circumstances, the use of ethylene glycols permitting the use of the embodiment already described.

In order to dehydrate a crude dioxane mixture consisting of 76.5% of dioxane, 20% of water, 3% of 2-methyldioxolane and 0.5% of acetaldehyde using ethylene glycol as solvent the mixture is continuously supplied to the tenth to fifteenth tray of a distillation column having a total of thirty to sixty trays and operating at atmospheric pressure. 2.4 to 5 kg of ethylene glycol per kg of crude dioxane mixture having a water content of less than 0.1% is continuously supplied from five to seven trays below the top of the column; the solvent is supplied in liquid form preferably at the temperature of the feed tray, i.e. 100° to 120°C. The amount of heat to be supplied to the bottoms of the column is from 300 to 700 kcal per kg of crude dioxane mixture. The reflux ratio to be set up at the top of the column is determined from the amount withdrawn at the top, the heat supplied to the bottoms and the enthalpy of the solvent stream.

Operating conditions for distillative dehydration of the mixture of ethylene glycol and water withdrawn from the bottoms and for refining the crude dioxane substantially freed from water obtained at the top of the column will be obvious to those skilled in the art so that a complete description may be dispensed with here.

The operation conditions should be appropriately modified when another solvent is used instead of the ethylene glycol described herein by way of example.

The following Examples illustrate the invention.

EXAMPLE 1

560 g/hour of crude dioxane containing 16.7% of water and 3.5% of lower boiling secondary components is supplied at a temperature of 70°C to the seventh tray of a column having a diameter of 50 mm and thirty trays. 2690 g/hour of ethylene glycol haviing a water content of 0.1% and a temperature of 120°C is supplied to the twenty-sixth tray of the column. 452 g/hours of crude dioxane is withdrawn at the top and 2645 g/hour is returned as a reflux at a temperature of 78°C. The temperature at the top is 97°C and the bottoms temperature is 167°C. Analysis of the overhead product gives a water content of 1.96% and the discharge from the bottoms contains 1.1% of dioxane.

EXAMPLE 2

560 g/hour of crude dioxane of the same composition as in Example 1 at a temperature of 40°C and 2680 g/hour of ethylene glycol at a temperature of 41°C are supplied to the same apparatus as in Example 1. The amount withdrawn at the top is 444 g/hour and the amount of reflux is 233 g/hour. The top temperature is 101°C and the bottoms temperature is 166°C. Analysis of the overhead product gives a water content of 1.5%; analysis of the bottoms product gives a dioxane content of 1.2%.

We claim:
1. A process for the recovery of substantially anhydrous dioxane from a reaction mixture containing dioxane and minor amounts of water, 1-methyldioxolane and acetaldehyde as impurities which comprises feeding dioxane containing minor amounts of water, 1-methyldioxolane and acetaldehyde as impurites to the middle portion of an extractive distillation column, also feeding to the top of said column a solvent selected from the group consisting of ethylene glycol, diethylene glycol, triethylene glycol, propylene glycol, dipropylene glycol, tripropylene glycol, propanetriol, propanediol, butanediol, a mono-lower alkanolamine, a di-lower alkanolamine, a tri-lower alkanolamine, and mixtures thereof at proportions of said solvent to dioxane in the range of 0.1:1 to 100:1, distilling off as overhead from said column substantially anhydrous dioxane plus the 1-methyldioxolane and acetaldehyde impurities, removing as bottoms from said column said solvent and most of the water impurity, and distilling said overhead to recover substantially pure dioxane.

2. A process as claimed in claim 1 wherein said solvent is one of said glycols.

3. A process as claimed in claim 1 wherein said solvent is one of said lower alkanolamines.

\* \* \* \* \*